US011261158B2

(12) United States Patent
Piisola et al.

(10) Patent No.: US 11,261,158 B2
(45) Date of Patent: Mar. 1, 2022

(54) SYNTHESIS OF 2-INDOLINONE DERIVATIVES

(71) Applicant: Fermion Oy, Espoo (FI)

(72) Inventors: Antti Piisola, Espoo (FI); Jan Tois, Espoo (FI)

(73) Assignee: FERMION OY, Espoo (FI)

( * ) Notice: Subject to any disclaimer, the term of this patent is extended or adjusted under 35 U.S.C. 154(b) by 9 days.

(21) Appl. No.: 16/763,685

(22) PCT Filed: Nov. 2, 2018

(86) PCT No.: PCT/FI2018/050799
§ 371 (c)(1),
(2) Date: May 13, 2020

(87) PCT Pub. No.: WO2019/097112
PCT Pub. Date: May 23, 2019

(65) Prior Publication Data
US 2020/0299275 A1 Sep. 24, 2020

(30) Foreign Application Priority Data

Nov. 17, 2017 (FI) ..................... 20176028

(51) Int. Cl.
C07D 209/34 (2006.01)
C07D 403/12 (2006.01)

(52) U.S. Cl.
CPC ......... C07D 209/34 (2013.01); C07D 403/12 (2013.01)

(58) Field of Classification Search
CPC .................................................. C07D 209/34
See application file for complete search history.

(56) References Cited

U.S. PATENT DOCUMENTS

| 6,762,180 | B1 | 7/2004 | Roth et al. |
| 8,304,541 | B2 | 11/2012 | Merten et al. |
| 2010/0075952 | A1 | 3/2010 | Chotang et al. |
| 2015/0284327 | A1 | 10/2015 | Rao et al. |
| 2016/0257648 | A1 | 9/2016 | Rao et al. |
| 2017/0174625 | A1 | 6/2017 | Xu |
| 2018/0064684 | A1 | 3/2018 | Wang et al. |
| 2018/0215735 | A1 | 8/2018 | Meca |

FOREIGN PATENT DOCUMENTS

| CN | 104844499 A | 8/2015 |
| CN | 105001143 A | 10/2015 |
| CN | 105418483 A | 3/2016 |
| CN | 105461609 A | 4/2016 |
| CN | 105712923 A | 6/2016 |
| CN | 105837493 A | 8/2016 |
| CN | 106432042 A | 2/2017 |
| CN | 106467500 A | 3/2017 |
| CN | 106748960 A | 5/2017 |
| WO | 0127081 A1 | 4/2001 |
| WO | 2004013099 A1 | 2/2004 |
| WO | 2007003934 A2 | 1/2007 |
| WO | 2007141283 A2 | 12/2007 |
| WO | 2009071523 A1 | 6/2009 |
| WO | 2009071524 A2 | 6/2009 |
| WO | 2012068441 A2 | 5/2012 |
| WO | 2016178064 A1 | 11/2016 |
| WO | 2017016530 A1 | 2/2017 |

OTHER PUBLICATIONS

Cantagrel, et al., "Iron Trichloride-Promoted Cyclization of o-Alkynylaryl Isocyanates: Synthesis of 3-(Chloromethylene)oxindoles", Organic Letters, vol. 11, No. 19, 2009, pp. 4262-4265, with supporting information.
Doroodmand, et al., "Sulfonated multiwalled carbon nanotubes (MWCNTa) as a new, efficient, and recyclable heterogeneous nanocatalyst for the synthesis of amines", Canadian Journal of Chemistry, vol. 90, Issue 8, 2012, pp. 701-707, with CA Abstract.
Fustero et al., "An Efficient and Simple Entry to N-Substituted—Enamino Acid Derivatives from 2-Alkyl-2-oxazolines and 2-Alkyl-2-thiazolines", J. Org. Chem., 1996, pp. 8849-8859.
Hennessy et al., "Synthesis of Substituted Oxindoles from α-Chloroacetanilides via Palladium-Catalyzed C—H Functionalization", J. Am. Chem. Soc., 2003, pp. 1-27, with supporting information.
Hilberg, et al., "BIBF 1120: Triple Angiokinase Inhibitor with Sustained Receptor Blockade and Good Antitumor Efficacy", Cancer Res., 68:, Jun. 15, 2008, pp. 4774-4783.
International Search Report (PCT/ISA/210) dated Jan. 14, 2019, by the Finland Patent Office as the International Searching Authority for International Application No. PCT/FI2018/050799.
Lu, et al., "Assembly of 3-Acyloxindoles via CuI/L-Proline-Catalyzed Intramolecular Arylation of—Keto Amides", Organic Letters, vol. 8, No. 26, 2006, pp. 6115-6118.
Roth et al., "Design, Synthesis, and Evaluation of Indolinones as Triple Angiokinase Inhibitors and the Discovery of a Highly Specific 6-Methoxycarbonyl-Substituted Indolinone (BIBF 1120)", Journal of Medicinal Chemistry, vol. 52, No. 14, 2009, pp. 4466-4480.
Sharma et al., "Synthesis, Characterization and Biological Activities of Some New Hypophosphorous Adducts of Acidhydrazones Derived from 2-[(N-benzoyl)-2,5-dichloroanilido]acetohydrazide", Asian Journal of Chemistry, vol. 24, No. 3, 2012, pp. 1271-1275.
Van Dijk, et al., "Facile Synthesis of Phosphaamidines and Phosphaamidinates using Nitrilium Ions as an Imine Synthon", Angew. Chem. Int. Ed., 53, 2014, pp. 9068-9071.
Walkup et al., "Efficient Asymmetric Synthesis of the $C_9$—$C_{21}$ Portion of the Aplysiatoxin and Oscillatoxin Marine Natural Products", J. Org. Chem., vol. 63, No. 24, 1998, pp. 9113-9116.
Würtz, et al., "Palladium-Catalyzed Oxidative Cyclization of N-Aryl Enamines: From Anilines to Indoles", Angew. Chem. Int. Ed., 47, 2008, pp. 7230-7233.

(Continued)

Primary Examiner — Emily A Bernhardt
(74) Attorney, Agent, or Firm — Buchanan Ingersoll & Rooney PC

(57) ABSTRACT

The present disclosure relates to a preparation method of methyl (E)-1-acetyl-3-(methoxy(phenyl)methylene)-2-oxoindoline-6-carboxylate from methyl 2-oxoindoline-6-carboxylate using high reaction temperatures and a reaction solvent enabling azeotropic removal of acetic acid during the reaction.

14 Claims, No Drawings

(56) References Cited

OTHER PUBLICATIONS

Xie et al., "CuI/L-Proline-Catalyzed Coupling Reactions of Aryl Halides with Activated Methylene Compounds", Organic Letters, vol. 7, No. 21, 2005, pp. 4693-4695.
Zhou et al., "Design, synthesis and pharmacological evaluation of 6,7-disubstituted-4-phenoxyquinoline derivatives as potential anti-tumor agents", Bioorganic Chemistry, 57, 2014, pp. 30-42.
International Search Report (PCT/ISA/210) dated Jan. 14, 2019, by the European Patent Office as the International Searching Authority for International Application No. PCT/FI2018/050799.

SYNTHESIS OF 2-INDOLINONE DERIVATIVES

FIELD OF THE INVENTION

The present invention relates to a process for the manufacturing of methyl (E)-1-acetyl-3-(methoxy(phenyl)methylene)-2-oxoindoline-6-carboxylate, which is an important intermediate in the preparation of biologically active molecules, especially the active pharmaceutical ingredient nintedanib, used in pharmaceuticals.

BACKGROUND OF THE INVENTION

Nintedanib esylate, (Z)-methyl 3-(((4-(N-methyl-2-(methylpiperazin-1-yl)acetamido)phenyl)amino)(phenyl) methylene)-2-oxoindoline-6-carboxylate ethanesulfonate, having the formula I

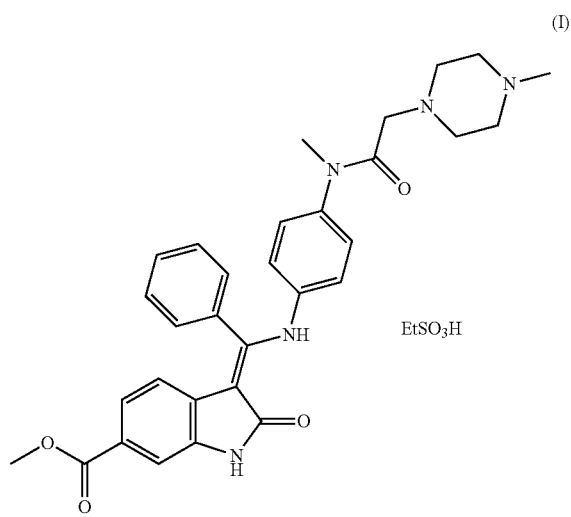

is a triple angiokinase inhibitor effective for the treatment of idiopathic pulmonary fibrosis. In combination with docetaxel, nintedanib esylate has been used for treatment of some types of non-small-cell lung cancer (*Cancer Res.*, 2008, 68, 4774-4782; *J. Med. Chem.*, 2009, 52, 4466-4480). The compound and its synthesis have, for example, been disclosed in the following patent applications: WO 01/27081, WO 2004/013099, WO 2009/071523, and WO 2009/071524.

WO 01/27081 discloses intermediates and process for the synthesis of 6-methoxycarbonyl-, and 6-ethoxycarbonyl-substituted indolinone derivatives, e.g. nintedanib, including preparation of methyl (E)-1-acetyl-3-(ethoxy(phenyl)methylene)-2-oxoindoline-6-carboxylate, the ethoxy-analogue of the methyl (E)-1-acetyl-3-(methoxy(phenyl)methylene)-2-oxoindoline-6-carboxylate intermediate. The ethoxy-analogue was prepared by treating methyl 2-oxoindoline-6-carboxylate with triethyl orthobenzoate and a 21.75 equivalents excess of acetic anhydride at 110° C. After complete solvent removal, re-crystallization of the evaporation residue from petroleum ether and drying the intermediate was obtained in 61% yield.

Roth et al., *J. Med. Chem.* 2009, 52, 4466-4480, describe a stepwise procedure for large scale synthesis. Methyl 2-oxoindoline-6-carboxylate was treated with 17.6 equivalents of acetic anhydride for eight hours at 130° C. After cooling the precipitated methyl 1-acetyl-2-oxoindoline-6-carboxylate was isolated in 73% yield, after which it was further reacted with trimethyl orthobenzoate in acetic anhydride at 120° C. for six hours. After completion of the reaction the mixture was concentrated to dryness and the residue was triturated with petroleum ether. After filtration and drying the methyl (E)-1-acetyl-3-(methoxy(phenyl) methylene)-2-oxoindoline-6-carboxylate was obtained in 56% yield. The combined yield of this two-isolation procedure was 40.9%.

In WO 2009/071523 an improved three-isolation process is disclosed. First the methyl 2-oxoindoline-6-carboxylate was N-chloroacetylated with chloroacetic anhydride in toluene at reflux for three hours. After cooling and methylcyclohexane treatment methyl 1-(2-chloroacetyl)-2-oxoindoline-6-carboxylate was isolated in 93.5% yield. The obtained chloroacetylated intermediate was further treated with trimethyl orthobenzoate in toluene in the presence of acetic anhydride. After completion of the reaction the methyl (E)-1-(2-chloroacetyl)-3-(methoxy(phenyl)methylene)-2-oxoindoline-6-carboxylate was isolated in 91.7% yield. After a base catalyzed chloroacetyl cleavage methyl (E)-3-(methoxy(phenyl)methylene)-2-oxoindoline-6-carboxylate was isolated in 94.6% yield. The combined yield of this three-step process was 81%.

Although the above-mentioned patent applications already describe a process for the manufacture of nintedanib there remains interest in developing other versatile and facile processes for the manufacture of intermediates useful for the synthesis of said drug substance as the known methods may not be readily adapted for use on industrial scale. Particularly problematic are evaporations to dryness, but also using toxic reagents such as chloroacetic anhydride and costs involved in complex multistep processes.

Now the inventors have discovered that methyl (E)-1-acetyl-3-(methoxy(phenyl)methylene)-2-oxoindoline-6-carboxylate can be obtained in high yield and sufficient purity with no need for intermediate isolation and with great operational simplicity. The key to this improvement is the introduction of a solvent to the N-acetylation of methyl 2-oxoindoline-6-carboxylate with acetic anhydride. This change greatly improves the selectivity of the reaction and enables partial removal of the formed acetic acid by azeotropic distillation prior to the treatment with trimethyl orthobenzoate. The volatiles generated during the reaction with trimethyl orthobenzoate are distilled off and sufficiently pure methyl (E)-1-acetyl-3-(methoxy(phenyl)methylene)-2-oxoindoline-6-carboxylate is obtained directly by filtration, without the need for tedious evaporations to dryness and recrystallizations or triturations.

SUMMARY OF THE INVENTION

The present invention is directed to a preparation method of methyl (E)-1-acetyl-3-(methoxy(phenyl)methylene)-2-oxoindoline-6-carboxylate from methyl 2-oxoindoline-6-carboxylate. It has been noticed that if the N-acetylation reaction and the enolether formation is carried out in a high boiling aromatic hydrocarbon solvent, which is capable of forming azeotropes with acetic acid, the formed acetic acid can be removed during the reaction stages, thus preventing the acetic acid induced decomposition of trimethyl orthobenzoate to methyl benzoate. This way the precipitated product can be directly isolated from the reaction mixture and no distillation to dryness or recrystallization or additional purification e.g. by chromatographic methods as used in the prior art are needed to achieve the product in high yield and purity.

DETAILED DESCRIPTION OF THE INVENTION

It was surprisingly found that significant benefits can be achieved with the process of the invention for the manufacture of methyl (E)-1-acetyl-3-(methoxy(phenyl)methylene)-2-oxoindoline-6-carboxylate, like improved yields, reduced raw material costs and operational simplicity. In addition, the process is suitable for larger industrial scale as in the present process only one isolation step is needed and distillations to dryness could be omitted.

The process in accordance with the present invention is shown in the following general synthesis scheme 1.

Scheme 1.

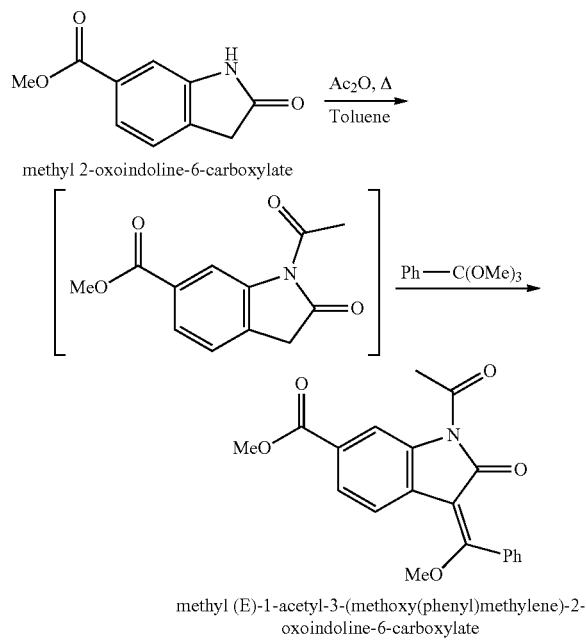

methyl 2-oxoindoline-6-carboxylate methyl (E)-1-acetyl-3-(methoxy(phenyl)methylene)-2-oxoindoline-6-carboxylate Characteristic features of the invention are presented in the appended claims.

The term "desired conversion" as used herein refers to over 90% conversion.

The term "reflux" as used herein refers to a chemical process wherein a portion of the product stream may be returned to the process.

The term "reflux temperature" as used herein means the temperature at which the solvent or solvent system refluxes or boils.

The term "elevated temperature" as used herein means any temperature above room temperature (i.e. above 25° C.).

In one aspect, the present invention provides a process for the preparation of methyl (E)-1-acetyl-3-(methoxy(phenyl) methylene)-2-oxoindoline-6-carboxylate comprising the steps of:
a) reacting methyl 2-oxoindoline-6-carboxylate with acetic anhydride in a high boiling aromatic hydrocarbon solvent to produce a methyl 1-acetyl-2-oxoindoline-6-carboxylate intermediate in solution,
b) distilling off parts of the reaction solvent mixture,
c) optionally adding fresh reaction solvent to the reaction vessel to compensate for the solvent distilled off,
d) reacting the methyl 1-acetyl-2-oxoindoline-6-carboxylate intermediate with trimethyl orthobenzoate,
e) distilling off parts of the reaction solvent mixture,
f) cooling the reaction mixture, and
g) isolating the solid product.

Another aspect of the present invention is the preparation of nintedanib using methyl (E)-1-acetyl-3-(methoxy(phenyl)methylene)-2-oxoindoline-6-carboxylate made by the method of the present invention as a starting material.

In accordance with the present invention methyl 2-oxoindoline-6-carboxylate is N-acetylated with acetic anhydride in a suitable solvent. The acetic anhydride is typically used in molar excess e.g. in 5-12 molar equivalents, more typically between 8-10 molar equivalents, per methyl 2-oxoindoline-6-carboxylate. Suitable solvents for the reaction are high boiling aromatic hydrocarbon solvents capable of forming azeotropes with acetic acid, such as toluene, xylene and chlorobenzene. Particularly preferred solvent is toluene. The volumes of solvents used are typically 3 to 7 volumes, preferably 3 to 5 volumes, even more preferably 5 volumes. The reaction is performed at elevated temperatures between 80-132° C., more typically between 115-120° C. when toluene is used as a solvent, and at 125-132° C. when xylene is used as solvent. The reaction time is 15-25 h, more preferably between 18-23 h in toluene and 4-6 h in xylene.

After consumption of the methyl 2-oxoindoline-6-carboxylate and formation of methyl 1-acetyl-2-oxoindoline-6-carboxylate a part of the formed acetic acid is distilled off. The distillation is conducted at atmospheric pressure or in vacuo. Typically 1-4 volumes of solvents are distilled off, more typically 2-3 volumes, even more typically 2 volumes. The distilled volumes are replaced by fresh solvent. Operating in the described manner the amount of harmful acetic acid can be efficiently diminished and better yield is obtained from the reaction between methyl 1-acetyl-2-oxoindoline-6-carboxylate and trimethyl orthobenzoate.

The reaction between methyl 1-acetyl-2-oxoindoline-6-carboxylate and trimethyl orthobenzoate is performed at elevated temperatures. Elevated temperature is preferably between 100 and 140° C., more preferably 110° C. to 130° C. The trimethyl orthobenzoate is added to the heated reaction rapidly as one portion, it is typically used in molar excess e.g. in 2.5-6 molar equivalents, more typically between 3-4 molar equivalents, per methyl 2-oxoindoline-6-carboxylate. If needed, an additional amount of trimethyl orthobenzoate can be added to the reaction also at later stage. During the reaction between the formed methyl 1-acetyl-2-oxoindoline-6-carboxylate and trimethyl orthobenzoate solvents are distilled off. Typically 5 to 8 volumes of volatiles in respect of methyl 2-oxoindoline-6-carboxylate, preferably 6-8 volumes of volatiles are distilled of during the reaction. The desired conversion, meaning that over 90% of the methyl 1-acetyl-2-oxoindoline-6-carboxylate intermediate is consumed, is obtained in 2-6 hours, more preferably in 3-4 hours.

As mentioned above it was discovered that the acetic acid has a considerably negative influence on the reaction between methyl 1-acetyl-2-oxoindoline-6-carboxylate and trimethyl orthobenzoate. On the other hand, acetic anhydride is needed for trimethyl orthobenzoate activation. When the acetic anhydride activates the trimethyl orthobenzoate and the activated species reacts with methyl 1-acetyl-2-oxoindoline-6-carboxylate acetic acid is formed which induces the decomposition of trimethyl orthobenzoate to methyl benzoate.

Thus, another aspect of the present invention is removal of acetic acid, formed during the activation of trimethyl orthobenzoate, by azeotropic distillation.

The present invention is further illustrated with the following non-limiting examples.

EXAMPLES

Example 1. Methyl (E)-1-acetyl-3-(methoxy(phenyl)methylene)-2-oxoindoline-6-carboxylate Methyl 2-oxindoline-6-carboxylate (20 g, 105 mmol) was charged to the reaction vessel. The vessel was equipped with thermometer, stirrer and condenser. Toluene (100 ml, 5 vol) was added followed by acetic anhydride (90 ml, 954 mmol) and the mixture was heated to reflux (115-118° C.). Reflux was continued for 18 hours and a sample was analyzed by HPLC for methyl 2-oxindoline-6-carboxylate (nmt 2.0 a-%). When the methyl 2-oxindoline-6-carboxylate was consumed 40 ml (2 vol) of solvent was distilled off followed by addition of fresh toluene (40 ml, 2 vol). Trimethyl orthobenzoate (53.9 ml, 314 mmol) was added to the boiling reaction during a couple of minutes maintaining the temperature above 110° C. After the addition was complete distillation began and the temperature of the reaction mixture was above 120° C. Eight volumes (160 ml) of solvents were distilled of after which the reaction temperature was adjusted between 110-115° C. The reflux was continued for two hours and precipitation of methyl (E)-1-acetyl-3-(methoxy(phenyl)methylene)-2-oxoindoline-6-carboxylate began during the reaction. According to HPLC-chromatogram 93.6% conversion was achieved. The reaction mixture was allowed to cool to room temperature during 5 hours, and then further cooled to 0° C. and stirred for two hours at 0° C. The precipitate was filtered and washed with EtOAc (2×20 ml, 2×1 vol) and dried in vacuum oven at 60° C. for 16 hours to obtain the product (33.99 g, 90.85%, 98.36 a-%) as tan powder. $^1$H NMR (400 MHz, DMSO-$d_6$): δ 8.89 (dd, J=1.5 Hz, J=0.6 Hz, 1H), 8.0 (dd, J=8.0 Hz, J=1.6 Hz, 1H), 7.94 (dd, J=8.1 Hz, J=1.6 Hz, 1H), 7.69-7.53 (m, 3H), 7.48-7.33 (m, 2H), 3.93 (s, 3H), 3.76 (s, 3H), 2.57 (s, 3H). $^{13}$C NMR (100 MHz, DMSO-$d_6$): δ 171.6, 171.3, 167.3, 167.2, 136.8, 131.0, 130.9, 129.1, 128.8, 128.5, 128.1, 126.5, 122.6, 116.7, 106.3, 57.9, 52.2, 27.0.

Example 2. Methyl (E)-1-acetyl-3-(methoxy(phenyl)methylene)-2-oxoindoline-6-carboxylate Methyl 2-oxindoline-6-carboxylate (20 g, 105 mmol) was charged to the reaction vessel. The vessel was equipped with thermometer, stirrer and condenser. Xylene (100 ml, 5 vol) was added followed by acetic anhydride (90 ml, 954 mmol) and the mixture was heated to 130° C. The heating was continued for 5 hours. 40 ml (2 vol) of solvent was distilled of followed by addition of fresh xylene (40 ml, 2 vol). Trimethyl orthobenzoate (53.9 ml, 314 mmol) was added to the reaction at 120° C. followed by heating to 130-135° C. Six volumes (120 ml) of solvents were distilled of and the mixture was seeded and allowed to cool to room temperature during two hours. The mixture was further cooled to 0° C. and stirred for two hours at 0° C. The product was filtered and washed with EtOAc (2×20 ml, 2×1 vol) and dried in vacuum oven at 70° C. for 18 hours. The weight of tan powder was 31.27 g (79.29%, 93.20 a-%).

Example 3. Methyl (Z)-3-(((4-(N-methyl-2-(4-methylpiperazin-1-yl)acetamido)phenyl)amino)(phenyl)methylene)-2-oxoindoline-6-carboxylate A heterogeneous mixture of methyl (E)-1-acetyl-3-(methoxy(phenyl)methylene)-2-oxoindoline-6-carboxylate (25 g), N-(4-aminophenyl)-N-methyl-2-(4-methylpiperazin-1-yl)acetamide (22.4 g, for preparation, see e.g. U.S. Pat. No. 6,762,180 B1 or U.S. Pat. No. 8,304,541 B2), methanol (200 ml) and N,N-dimethylformamide (50 ml) was stirred and heated to reflux for 3-4 hours. A clear brown solution was obtained. A sample was drawn and analyzed for the presence of the limiting starting material (nmt 1%). Piperidine (10.5 ml) was then added and the mixture was stirred under reflux for another 30-60 minutes. The product precipitated out during the stirring. The reaction mixture was analyzed for the intermediate and once nmt 1% remained as determined by HPLC, the mixture was cooled to 0° C. and stirred from 2 h to overnight. The solids were isolated by filtration and washed twice with methanol (75 ml per wash), then dried in a vacuum oven at 40° C. overnight to obtain methyl (Z)-3-(((4-(N-methyl-2-(4-methylpiperazin-1-yl)acetamido)phenyl)amino)(phenyl)methylene)-2-oxoindoline-6-carboxylate (33.7 g, 88%, 99.8 a-%) as a bright yellow solid.

Example 4. Nintedanib Esylate

A suspension of (Z)-3-(((4-(N-methyl-2-(4-methylpiperazin-1-yl)acetamido)phenyl)amino)(phenyl)methylene)-2-oxoindoline-6-carboxylate (75 g) in methanol (500 ml) and water (6 ml) was heated to 60° C. and ethanesulfonic acid (70 w-% aq., 18.3 ml) was added to the mixture. A clear solution was obtained. The solution was cooled to 50° C., seeded and 2-propanol (500 ml) was added while maintaining the temperature at 50° C. The resulting suspension was cooled to 0° C. and stirred for 1-2 h, then isolated by filtration and washed with 2-propanol (300 ml). The solids were dried in a vacuum oven at 40° C. overnight to obtain Nintedanib esylate (84.5 g, 89%, 99.8 a-%) as a bright yellow solid.

The invention claimed is:
1. A process for preparation of methyl (E)-1-acetyl-3-(methoxy(phenyl)methylene)-2-oxoindoline-6-carboxylate, the process comprising:
   a) reacting methyl 2-oxindoline-6-carboxylate with acetic anhydride in a high boiling aromatic hydrocarbon solvent to produce a methyl 1-acetyl-2-oxoindoline-6-carboxylate intermediate in solution as a reaction solvent mixture in a reaction vessel;
   b) distilling off parts of the reaction solvent mixture;
   c) optionally adding fresh reaction solvent to the reaction vessel to compensate for solvent distilled off;
   d) reacting the methyl 1-acetyl-2-oxoindoline-6-carboxylate intermediate with trimethyl orthobenzoate to produce a second reaction solvent mixture;
   e) distilling off parts of the second reaction solvent mixture;
   f) cooling the second reaction solvent mixture; and
   g) isolating a solid product of the second reaction solvent mixture, the solid product containing methyl (E)-1-acetyl-3-(methoxy(phenyl)methylene)-2-oxoindoline-6-carboxylate.

2. The process of claim 1, wherein the high boiling aromatic hydrocarbon solvent in step a) is toluene, xylene or chlorobenzene.

3. The process of claim 1, wherein the high boiling aromatic hydrocarbon solvent in step a) is toluene.

4. The process of claim 1, wherein a reaction temperature in step a) is between 80° C. and 132° C.

5. The process of claim 1, wherein an amount of solvent distilled off in step b) is 1-4 volumes of solvents in respect to an amount of methyl 2-oxindoline-6-carboxylate charged.

6. The process of claim 5, wherein the amount of solvent distilled off in step b) is 2-3 volumes in respect to the amount of methyl 2-oxindoline-6-carboxylate charged.

7. The process of claim 1, wherein an reaction temperature in step d) is between 100° C. and 140° C.

8. The process of claim 4, wherein the reaction temperature is a reflux temperature of the reaction solvent mixture.

9. The process of claim 1, wherein the distilling of the reaction solvent mixture in steps b) and e) comprises:
removing formed acetic acid by azeotropic distillation.

10. A process for preparation of nintedanib, comprising:
a) reacting methyl 2-oxoindoline-6-carboxylate with acetic anhydride in a high boiling aromatic hydrocarbon solvent to produce a methyl 1-acetyl-2-oxoindoline-6-carboxylate intermediate in solution as a reaction solvent mixture in a reaction vessel;
b) distilling off parts of the reaction solvent mixture;
c) optionally adding fresh reaction solvent to the reaction vessel to compensate for solvent distilled off;
d) reacting the methyl 1-acetyl-2-oxoindoline-6-carboxylate intermediate with trimethyl orthobenzoate to produce a second reaction solvent mixture;
e) distilling off parts of the second reaction solvent mixture;
f) cooling the second reaction solvent mixture;
g) isolating a solid product of the second reaction solvent mixture, the solid product comprising methyl (E)-1-acetyl-3-(methoxy(phenyl)methylene)-2-oxoindoline-6-carboxylate, and h) reacting the solid product comprising methyl (E)-1-acetyl-3-(methoxy(phenyl)methylene)-2-oxoindoline-6-carboxylate with N-(4-aminophenyl)-N-methyl-2-(4-methylpiperazin-1-yl)acetamide to produce nintedanib.

11. The process of claim 7, wherein the reaction temperature is a reflux temperature of the reaction solvent mixture.

12. The process of claim 1, comprising:
adding fresh reaction solvent to the reaction vessel to compensate for solvent distilled off in step b).

13. The process of claim 4, wherein the reaction temperature in step d) is a reflux temperature of the reaction solvent mixture.

14. The process of claim 4, wherein an reaction temperature in step d) is between 100° C. and 140° C.

* * * * *